(12) United States Patent
Matsen

(10) Patent No.: US 8,938,303 B1
(45) Date of Patent: Jan. 20, 2015

(54) RESTLESS LEG THERAPEUTIC DEVICE

(76) Inventor: Brandie Matsen, Basalt, ID (US)

(*) Notice: Subject to any disclaimer, the term of this patent is extended or adjusted under 35 U.S.C. 154(b) by 240 days.

(21) Appl. No.: 13/150,920

(22) Filed: Jun. 1, 2011

Related U.S. Application Data

(60) Provisional application No. 61/350,068, filed on Jun. 1, 2010.

(51) Int. Cl.
*A61N 1/00* (2006.01)
*A61N 1/36* (2006.01)
*A61N 1/04* (2006.01)

(52) U.S. Cl.
CPC ........... *A61N 1/36021* (2013.01); *A61N 1/0452* (2013.01)
USPC ................ 607/48; 607/46; 607/152; 607/149

(58) Field of Classification Search
CPC .. A61N 1/0424; A61N 1/0452; A61N 1/0476
USPC .................. 607/46, 48, 49, 148, 152, 149
See application file for complete search history.

(56) References Cited

U.S. PATENT DOCUMENTS

| | | | |
|---|---|---|---|
| 3,827,107 A * | 8/1974 | Moore | 24/16 R |
| 4,411,268 A | 10/1983 | Cox | |
| 4,580,569 A | 4/1986 | Petrofsky | |
| 4,832,033 A | 5/1989 | Maher et al. | |
| 5,643,332 A * | 7/1997 | Stein | 607/49 |
| 6,282,448 B1 * | 8/2001 | Katz et al. | 607/48 |
| 6,341,237 B1 * | 1/2002 | Hurtado | 607/148 |
| 6,445,955 B1 * | 9/2002 | Michelson et al. | 607/46 |
| 7,499,746 B2 | 3/2009 | Buhlmann et al. | |
| 2003/0065368 A1 | 4/2003 | van der Hoeven | |
| 2004/0236384 A1 | 11/2004 | Dar et al. | |
| 2004/0243196 A1 | 12/2004 | Campos et al. | |
| 2009/0048642 A1 * | 2/2009 | Goroszeniuk | 607/46 |

* cited by examiner

*Primary Examiner* — Michael Kahelin
*Assistant Examiner* — Mallika D Fairchild
(74) *Attorney, Agent, or Firm* — Robert C. Montgomery; Montgomery Patent & Design

(57) ABSTRACT

A therapeutic device for treating symptoms related to restless leg syndrome comprises a remote, a pair of pads, a plurality of electrodes, and a fastener assembly. The remote comprises a power source and an interface further comprising an ON/OFF switch and a method for providing variable power to the plurality of electrodes. Each pad comprises a brace-type fitting which fits around a user's afflicted area in a comfortable but secure manner. The plurality of electrodes comprises a number of electrodes affixed to the interior of each pad. A plurality of wires connects each electrode to the power source in the remote. The fastener assembly comprises a plurality of straps permanently attached to each pad, each disposed with fasteners to allow for the secure and comfortable affixation of the pads and electrodes to a user's desired area.

16 Claims, 6 Drawing Sheets

RESTLESS LEG THERAPEUTIC DEVICE

RELATED APPLICATIONS

The present invention was first described in and claims the benefit of U.S. Provisional Application No. 61/350,068 filed Jun. 1, 2010, the entire disclosure of which is incorporated herein by reference.

FIELD OF THE INVENTION

The present invention relates generally to apparatuses utilizing electrical stimulation for therapeutic purposes, and in particular, to a therapeutic electrical stimulation apparatus particularly adapted for use by persons suffering from restless leg syndrome (RLS).

BACKGROUND OF THE INVENTION

Many people suffer from restless leg syndrome, or RLS as it is commonly called. RLS is a medical condition in which an afflicted person has regular urges to move their legs in order to relieve uncomfortable internal sensations.

Movement of the legs typically stops or reduces these uncomfortable internal sensations, but this relief is generally very short-lived and the sensations quickly return when the legs stop moving. Many users afflicted with severe cases of RLS have turned to therapy, drugs, or even surgery to help rid their body of this affliction. Unfortunately, what has been found to work for some people produces little or no change in another, and only constant stimulation of the legs is known to work consistently.

One (1) known method for stimulating muscles in the field of medical therapy is the use of electrodes which apply weak electrical pulses to the surface of a user's skin in order to cause the underlying muscles to contract.

Various attempts have been made to provide automated electrical muscle stimulators for therapeutic use. Examples of these attempts can be seen by reference to several U.S. patents such as U.S. Pat. No. 4,411,268; U.S. Pat. No. 4,832,033; U.S. Pat. No. 6,341,237; and U.S. Pat. No. 7,499,746.

While these apparatuses fulfill their respective, particular objectives, each of these references suffer from one (1) or more of the aforementioned disadvantages. Many such apparatuses are not adapted for use on the legs. Many such apparatuses are designed for use in a dedicated therapy environment and are immobile, bulky, or expensive, thereby limiting their efficacy for personal use. Many such apparatuses are dedicated to particular rehabilitative uses and are not adapted to provide a simple level of stimulation desirable for people with RLS. Furthermore, many such apparatuses do not provide a desirable range of controls providing a minimum functionality for comfortable use by RLS patients but without unnecessary complexity that is undesirable for the particular task of mitigating RLS. Accordingly, there exists a need for a therapeutic device particularly adapted for persons suffering from RLS and without the disadvantages as described above. The development of the present invention substantially departs from the conventional solutions and in doing so fulfills this need.

SUMMARY OF THE INVENTION

In view of the foregoing references, the inventor recognized the aforementioned inherent problems and observed that there is a need for a restless leg therapeutic device that is simple and portable and that has features particularly adapted to users afflicted with RLS. Thus, the object of the present invention is to solve the aforementioned disadvantages and provide for this need.

To achieve the above objectives, it is an object of the present invention to provide electrical stimulation of a user's muscles particularly adapted to treat restless leg syndrome (RLS) or a similar ailment. The apparatus is positioned on the user's leg during use to stimulate muscle contraction with a plurality of electrodes.

Another object of the present invention is to provide adjustable positioning and configuration of the apparatus during use to accommodate different leg sizes and user preferences. The apparatus comprises an upper pad and a lower pad each having a plurality of electrodes. The upper and lower pads are connected with an adjustable length intermediate strap that allows the user to selectively vary the distance between the pads.

Yet still another object of the present invention is to accommodate users of different sizes by providing adjustable fastening and tightening for the upper and lower pads utilizing a pair of upper pad straps and a pair of lower pad straps, respectively.

Yet still another object of the present invention is to further secure an interior surface of each pad and the plurality of electrodes with a plurality of adhesive tacky surfaces that temporarily adhere to the user's skin. The tacky surfaces can be covered with a wax paper-type removable cover during periods of non-use in order to preserve the adhesive.

The tacky surfaces further ensure contact between the user's skin and the electrodes to ensure proper functioning of the apparatus during use.

Yet still another object of the present invention is to provide comfort and cushioning with a fabric layer disposed along an interior surface of the pads between the electrodes.

Yet still another object of the present invention is to allow a user to adjustably control operation of the electrodes during use using a handheld controller. The controller is wired to the electrodes and includes a replaceable or rechargeable battery power supply that also powers the electrodes.

Yet still another object of the present invention is to provide integral storage and protection for the controller within a pocket disposed along a front surface of the upper pad.

Yet still another object of the present invention is to provide the user with a plurality of basic controls for the electrodes including an operational switch for turning the electrodes on or off and increment and decrement buttons that allow the user to selectively control the intensity of the electrodes during use.

Yet still another object of the present invention is to provide an additional range of electrode-driven therapeutic functionality not associated with RLS including use on other body areas such as a torso or abdomen.

Yet still another object of the present invention is to provide a method of utilizing the device that provides a unique means of acquiring the apparatus, positioning the upper pad and lower pad on a desired location with the electrodes against the afflicted area, fastening the pads, using the operational switch and increment/decrement buttons to control the apparatus, placing the controller into the pocket for hands free use, contracting the muscles in the desired area on the user; and, utilizing the apparatus to provide relief from RLS or similar ailments in a manner which is simple, effective, and comforting.

Further objects and advantages of the present invention will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

Figure 1:
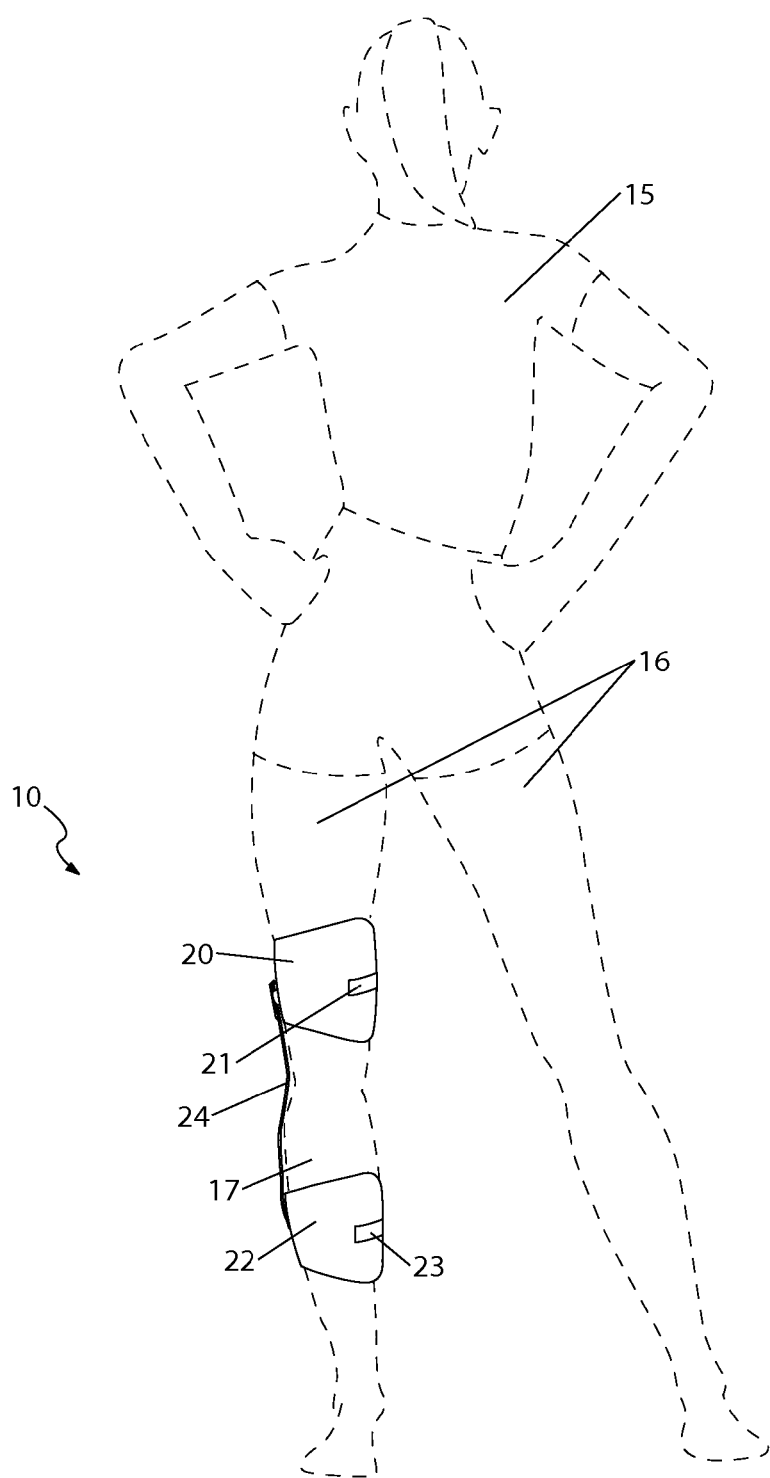
FIG. 1 is an environmental view of a restless leg therapeutic device 10, according to a preferred embodiment of the present invention.

DESCRIPTIVE KEY 10 restless leg therapeutic device
13 bicep
14 forearm
15 user
16 thigh
17 calf
18 torso
20 upper pad
21 upper pad strap
22 lower pad
23 lower pad strap
24 intermediate strap
25 fastening loop
26 securing means
27 aperture
30 electrode
35 wire
40 pocket
50 controller
51 operational switch
52 increment button
53 decrement button
54 battery
55 control module
56 electricity generator
57 battery compartment
60 cover

DETAILED DESCRIPTION OF THE PREFERRED EMBODIMENT

In accordance with the invention, the best mode is presented in terms of a preferred embodiment, herein depicted within FIGS. 1 through 6. However, the disclosure is not limited to a single described embodiment and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only one particular configuration may be shown and described for purposes of clarity and disclosure and not by way of limitation of scope.

The terms "a" and "an" herein do not denote a limitation of quantity, but rather denote the presence of at least one of the referenced items.

The present invention describes a restless leg therapeutic device (herein described as the "apparatus") 10, which provides an electrical muscle stimulator to treat restless leg syndrome (RLS) or a similar ailment. The apparatus 10 is preferably positioned on a leg portion of the user 15 to stimulate muscle contraction to the bothersome area via a plurality of electrodes 30 which are controlled via a controller 50. The apparatus 10 may also be positioned on a torso 18 portion (see FIG. 5) or an arm portion (see FIG. 6) without limiting the scope of the apparatus 10. The apparatus 10 is comprised of an upper pad 20 and a lower pad 22 which are attached to the user 15 with a securing means 26. The apparatus 10 alleviates the uncontrollable impulses to move one's body which is commonly associated with RLS.

Referring now to FIG. 1, an environmental view of the apparatus 10, according to the preferred embodiment of the present invention, is disclosed. The apparatus 10 is depicted herein as being positioned on a thigh 16 and on a calf 17 of the user 15 for illustration purposes only, it is known that other abovementioned areas (see FIGS. 5 and 6) may be utilized without limiting the scope of the apparatus 10. The upper pad 20 is depicted as being positioned on the afflicted thigh 16 area of a user 15 and fastened to said thigh 16 via an upper pad strap 21 (also see FIGS. 2 and 3). The lower pad 22 is depicted as being positioned on the afflicted calf 17 area of a user 15 and fastened to said calf 17 via a lower pad strap 23 (also see FIGS. 2 and 3). The upper and lower pads 20, 22 are attached on the body area such that a plurality of electrodes 30 is positioned against the afflicted area. The apparatus 10 generates impulses via the electrodes 30 to contract the muscles of the afflicted area which correspondingly relaxes said afflicted area and calms the RLS.

Figure 2:
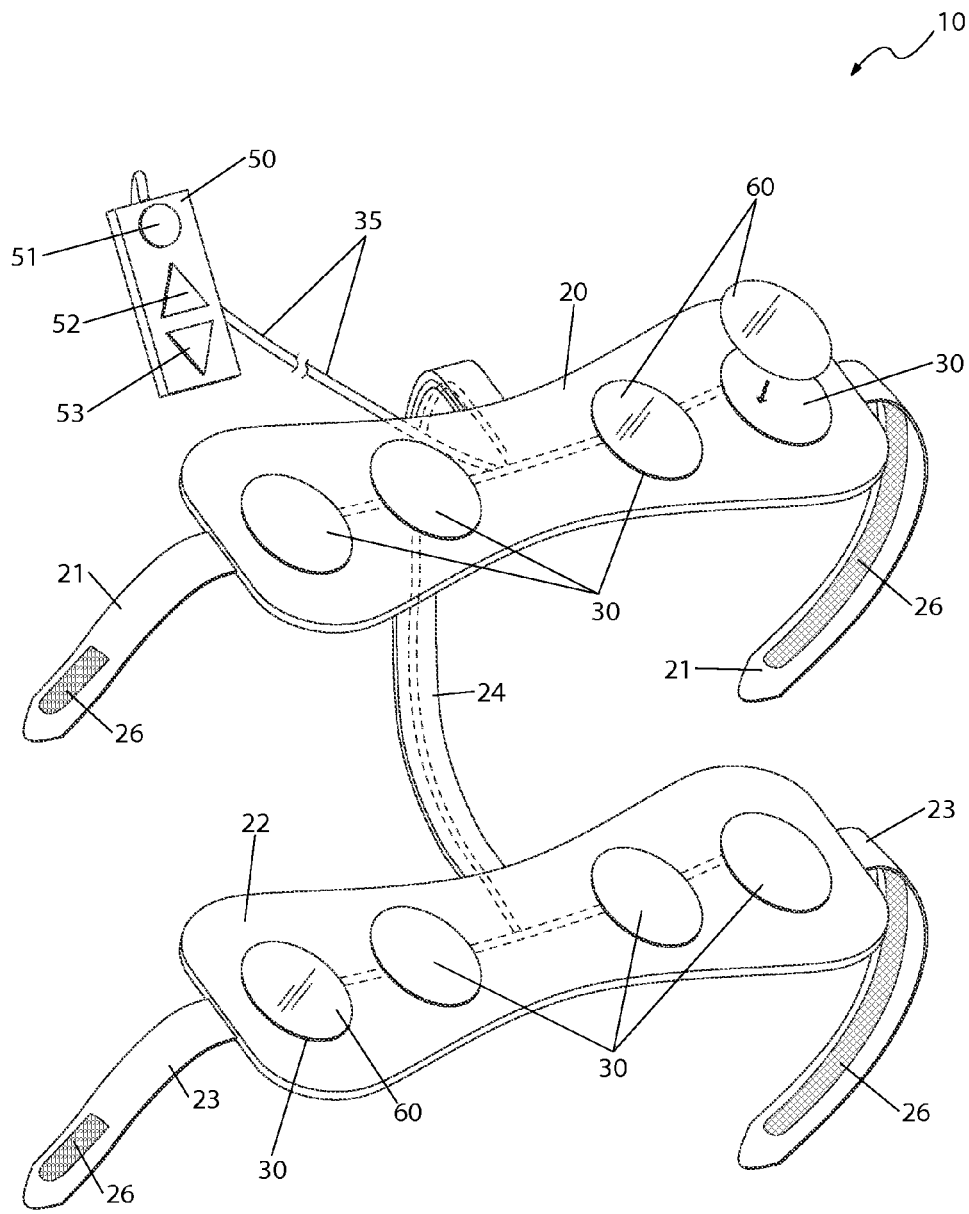
FIG. 2 is a rear perspective view of the restless leg therapeutic device 10, according to a preferred embodiment of the present invention.
Figure 3:
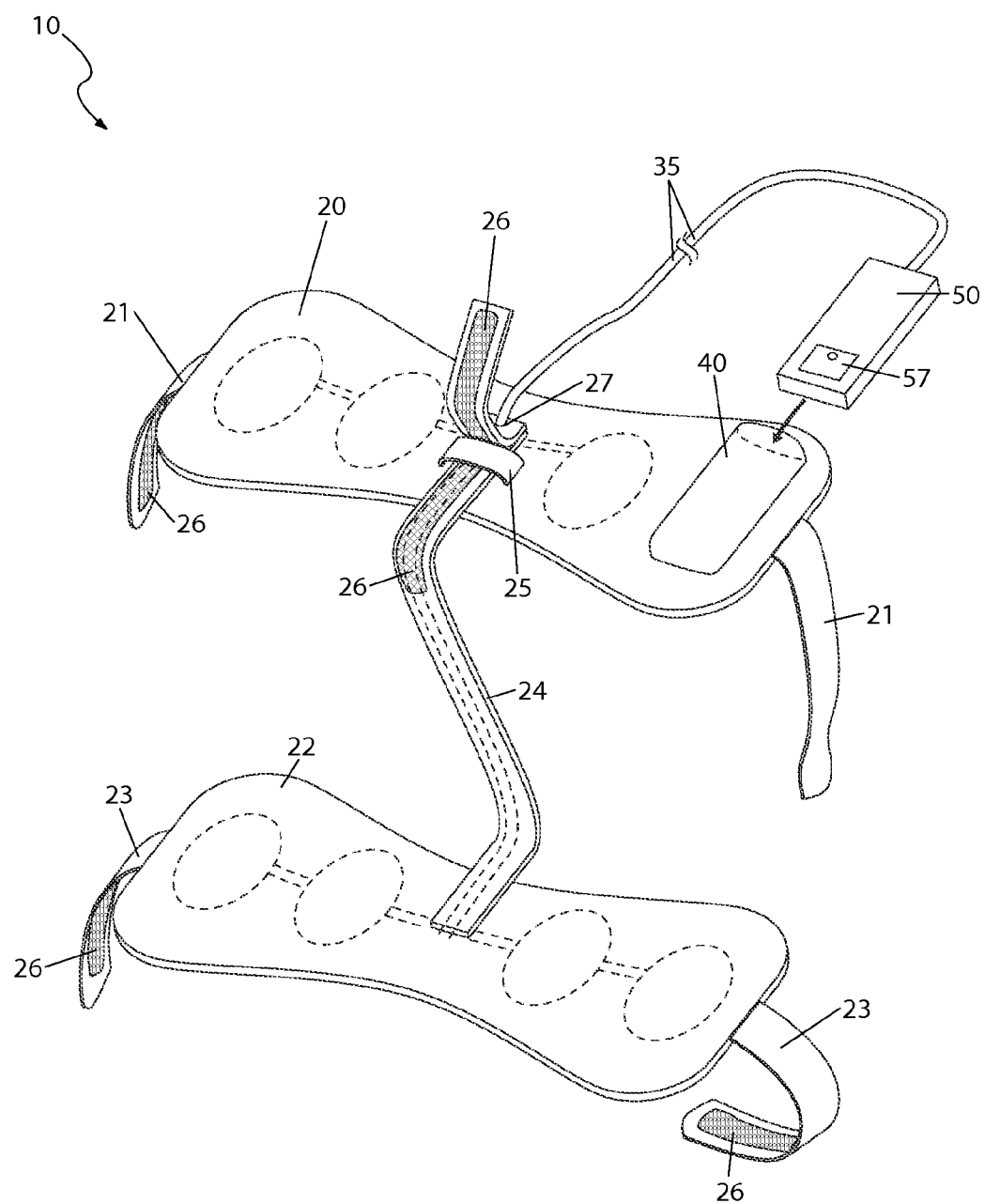
FIG. 3 is a front perspective view of the restless leg therapeutic device 10, according to a preferred embodiment of the present invention.

Referring now to FIG. 2, a rear perspective view of the apparatus 10 and FIG. 3, a front perspective view of the apparatus 10, according to the preferred embodiment of the present invention, are disclosed. The upper pad 20 and lower pad 22 comprise hourglass-shaped bodies which are utilized to encompass the RLS afflicted areas upon the user 15. A rear surface of the upper pad 20 and lower pad 22 (as depicted in FIG. 2) are positioned against the skin of the afflicted areas on the user 15 which enable a plurality of electrodes 30 to adhere to said skin and contract the desired muscles. The electrodes 30 are integrally molded between the respective pads 20, 22, yet an upper surface of said electrodes 30 are exposed from the rear surface of each said pad 20, 22 which enables them to be in-contact with the user's 15 afflicted area when in use. The upper surface of the electrodes 30 must be in contact with the user 15 to enable the muscle stimulation to conduct properly. The electrodes 30 comprise a tacky upper surface to temporarily adhere to the user 15. Each electrode 30 preferably comprises a wax paper-type removably replaceable cover 60 which comprises a circular-shape having a diameter able to fully cover the electrodes 30 to maintain the tacky surface while not in use, in a conventional manner, to enable said electrodes 30 to be reusable. Each electrode 30 is interconnected internally to each other via electrical wire 35 which is further connected to a controller 50 (see herein below). The controller 50 enables the user 15 to control the electrodes 30 to a desired setting. The upper pad 20 and lower pad 22 are comprised of a neoprene material, yet other elastic-type materials may be utilized without limiting the scope of the apparatus 10. The rear surface of the upper pad 20 and the rear surface of the lower pad 22 may comprise a terry cloth covering to provide a cushioning and comforting surface against the skin of the user 15 without limiting the functions of the apparatus 10.

The upper pad 20 and lower pad 22 comprise a securing means 26 to fasten the apparatus 10 to the user 15. The upper pad 20 comprises a pair of upper pad straps 21 attached to each opposing lateral perimeter edge of the upper pad 20. The upper pad straps 21 further include the securing means 26 to attach the upper pad 20 around the desired afflicted area on the user 15. The lower pad 22 comprises a pair of lower pad straps 23 attached to each opposing lateral perimeter edge of the lower pad 22. The lower pad straps 23 also include the securing means 26 which provides a means to attach the lower pad 22 around the desired afflicted area on the user 15. The straps 21, 23 are fabricated from a material similar to the pads 20, 22 and are attached to their respective areas via common sewing techniques. The straps 21, 23 comprise a length which is accommodating to various sized users 15 desired and positioning of the apparatus 10. The securing means 26 is preferably a common hook-and-loop-type fastener, yet other fastening devices may be utilized without limiting the scope of the apparatus 10.

The front surface of the upper pad 20 comprises a pocket 40 which provides a retaining member to retain the controller 50. The pocket 40 is depicted as being located on the upper pad 20 for illustration purposes only; it is known that other locations may be utilized without limiting the scope of the apparatus 10. The pocket 40 receives the controller 50 while the apparatus 10 is in-use or being stored. The pocket 40 includes an upper opening which receives the controller 50 and is preferably attached to the upper pad 20 along bottom and side edges via common sewing techniques.

The controller 50 comprises a rectangular body further comprising an operational switch 51, an increment button 52, a decrement button 53, a battery 54, and associated electrical and electronic components. The operational switch 51, increment button 52, and decrement button 53 are controlled via an internal control module 55 (see FIG. 4). The operational switch 51 activates and deactivates the apparatus 10 as desired by the user 15. The operational switch 51 is comprised of common pushbutton switch, yet other switching devices may be utilized without limiting the scope of the apparatus 10. The increment button 52 and decrement button 53 provide the user 15 with a means to control the intensity of an electricity generator 56 which causes electrical impulses to contract muscles on the user 15 (see FIG. 4). The buttons 52, 53 are also comprised of common pushbutton switches, yet other switching devices may be utilized without limiting the scope of the invention. The controller 50 is interconnected via wiring 35 to each electrode 30 which is further interconnected to the control module 55 and the electricity generator 56. Current is supplied to the controller 50 and concurrently the apparatus 10 via common user replaceable batteries 54 (see FIG. 4) which are accessed from a rear portion of the controller 50 via a battery compartment 57.

The apparatus 10 also comprises an intermediate strap 24 which provides a means to conceal the wiring 35 which also interconnects the upper pad 20 and the lower pad 22. The wiring passes through an aperture 27 of the intermediate strap 24, which then travels to each upper pad 20 and lower pad 22. The intermediate strap 24 is fastened to an intermediate front surface of the lower pad 22 via sewing techniques and is adjustably fastened to an intermediate front surface of the upper pad 20 via a perpendicularly orientated fastening loop 25. Side edges of the fastening loop 25 are attached to the upper pad 20 via sewing techniques which enables the intermediate strap 24 to pass through and secure upon itself via another hook-and-loop-type fastener securing means 26. This adjustable securing of the intermediate strap 24 adjusts the distance between the pads 20, 22 to correspond to various user 15 sizes and desired positioning of the apparatus 10. An upper portion of the intermediate strap 24 enables the wiring 35 which leads to the controller 50 to egress. The intermediate strap 24 is fabricated from a similar material as the pads 20, 22 and may also provide a surface area for placement of indicia such as, but not limited to: sports names/logos, personal names, symbols, pictures, and the like to further customize and personalize the apparatus 10.

Figure 4:
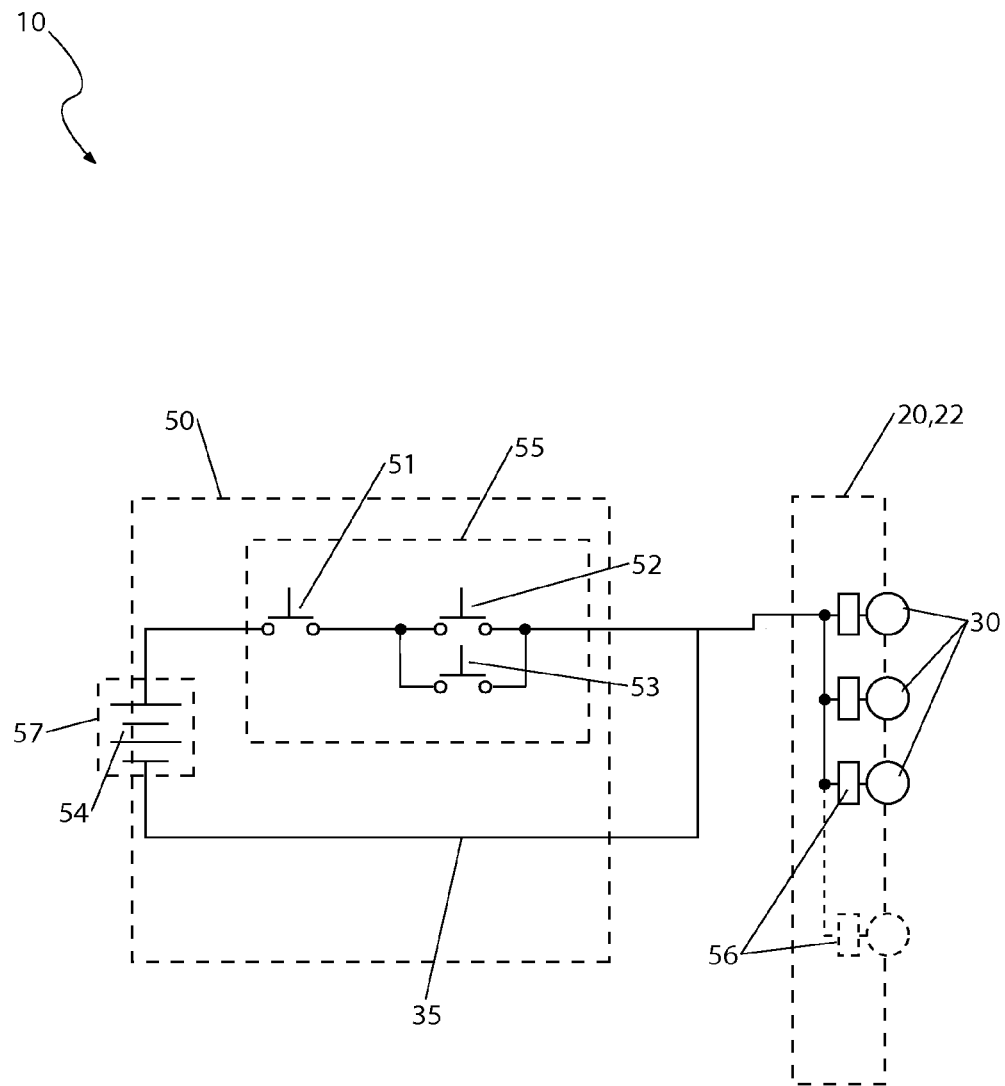
FIG. 4 is an electrical block diagram of the restless leg therapeutic device 10, according to a preferred embodiment of the present invention.

Referring now to FIG. 4, an electrical block diagram depicting the major electrical components of the apparatus 10, according to the preferred embodiment of the present invention, is disclosed. A current is supplied to the apparatus 10 via the battery 54 housed within the battery compartment 57 further within the controller 50. The battery 54 is a user replaceable electrochemical cell such which supplies an appropriate amount of current to power the apparatus 10. The battery 54 is interconnected to the control module 55 and concurrently the operational switch 51, increment button 52, and decrement button 53 via appropriately gauged electrical wire 35. The control module 55 comprises circuitry to manipulate the electrodes 30 via the input from the user 15. Current is then sent to the electricity generator 56 upon each electrode 30 which stimulates the desired muscle to contract. The range of the electricity generator 56 is common to those currently on the market with a voltage range of approximately twenty-five (25) volts, a safe current output, and a suitable frequency range. The electricity generator 56 enables the muscle to depolarize itself which concurrently and constantly contracts said muscle at a desired strength as determined via the buttons 52, 53, it is known that this procedure is common to many muscle stimulating devices existing in the field. The electrodes 30 provide an electrical conductor to enable contact with a nonmetallic portion such as the user's 15 skin. The contraction of the muscle is constantly repeated a desired amount of times until the user 15 remove each electrode 30 from the desired afflicted area and deactivates the apparatus 10 via the controller 50. The constant muscle contraction relaxes the muscles and alleviates the bothersome consequences of RLS.

Figure 5:
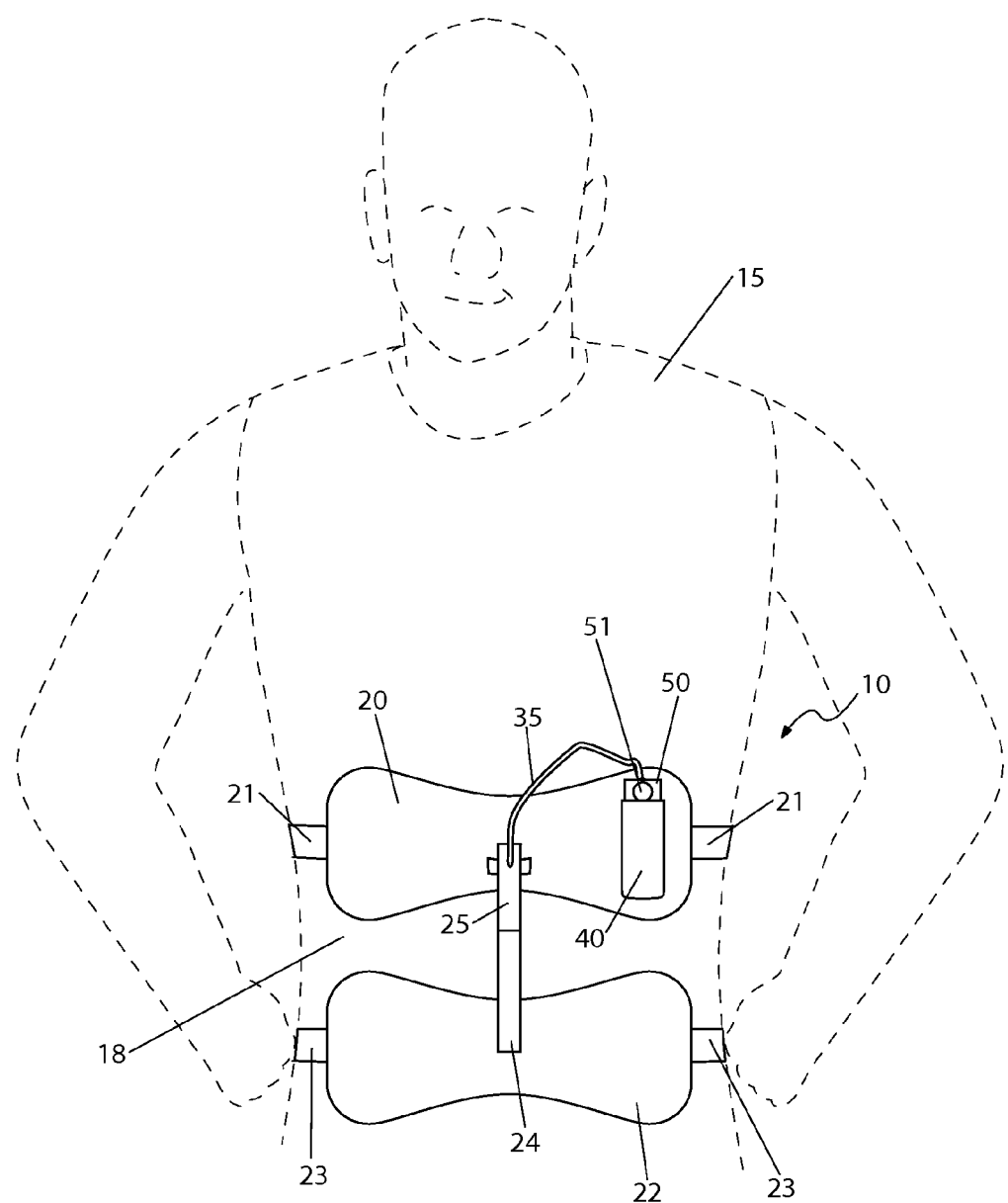
FIG. 5 is another environmental view of the restless leg therapeutic device 10 depicting placement upon a torso 18, according to an alternate method of use of the present invention; and, FIG. 6 is yet another environmental view of the restless leg therapeutic device 10 depicting placement upon a bicep 13 and a forearm 14, according to yet another alternate method of use of the present invention.
Figure 6:
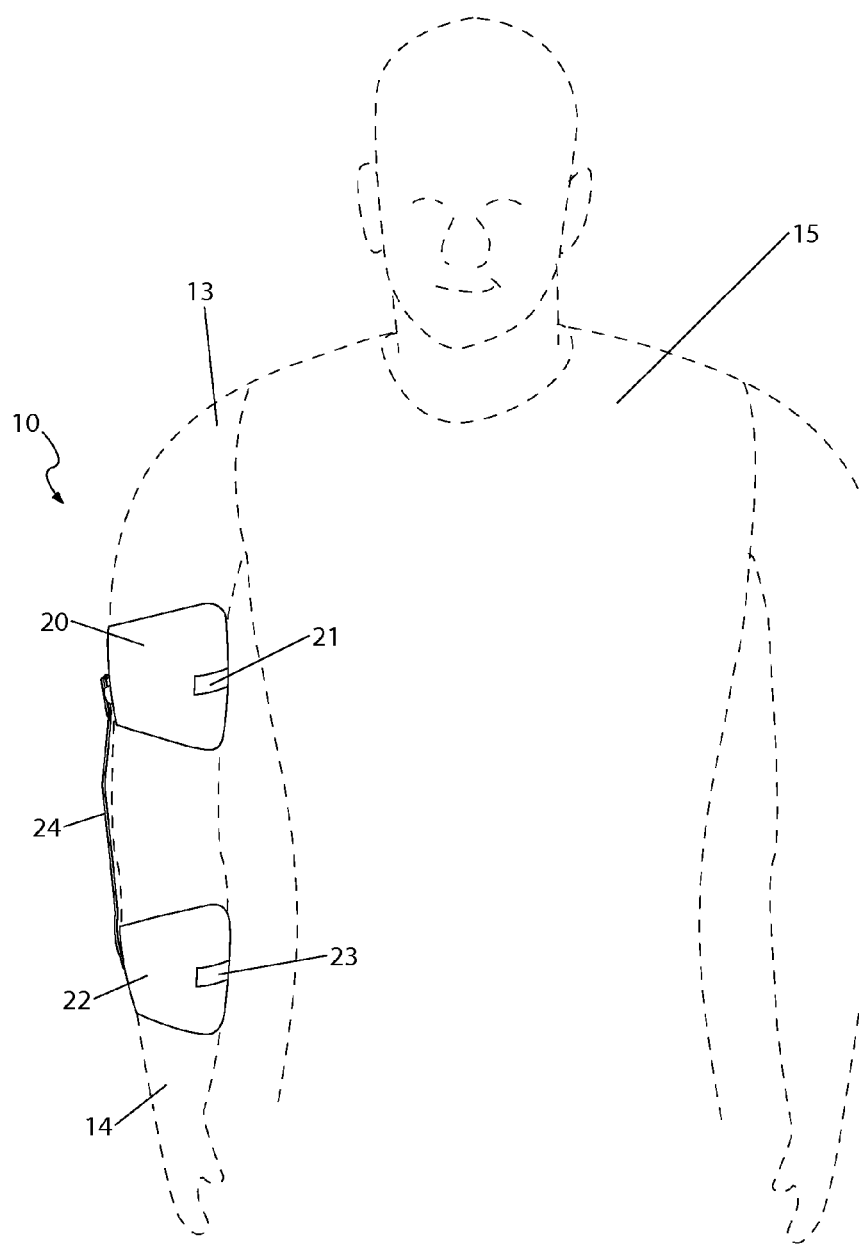

Referring now to FIG. 5, another environmental view of the apparatus 10 depicting placement upon a torso 18 and FIG. 6, yet another environmental view of the apparatus 10 depicting placement upon a bicep 13 and a forearm 14, according to alternate methods of use of the present invention, are disclosed. FIGS. 5 and 6 depict use of the apparatus 10 upon other body parts which are not affected by RLS, yet benefit from the muscle stimulation which said apparatus 10 produces. FIG. 5 depicts the apparatus 10 attached to the torso 18 of a user 15 which stimulates the abdominal muscles. Utilizing the apparatus 10 upon the torso 18 of the user 15 contributes in abdominal muscle enlargement. The upper pad 20 is orientated blow the user's 15 upper abdominal region and the lower pad 22 is orientated upon the lower abdominal region. The straps 21, 23 wrap around to a back region of the user 15 and attach via the securing means 26 as abovementioned. FIG. 6 depicts the apparatus 10 attached to the arm of a user 15 to stimulate the muscles of the bicep 13 and the forearm 14. The upper pad 20 is orientated upon the bicep 13 and the lower pad 22 is orientated upon the forearm 14. The upper pad strap 21 is fastened around the bicep 13 and the lower pad strap 23 is fastened around the forearm 14.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIG. 1.

The method of utilizing the apparatus 10 may be achieved by performing the following steps: acquiring the apparatus 10; positioning the upper pad 20 on a desired location on the user 15 with the rear surface placed against the skin of the user 15 such that the electrodes 30 are against the afflicted area; fastening the upper pad 20 around the desired area on the user 15 via the upper pad straps 21 and securing via the securing means 26; positioning the lower pad 22 on a desired location on the user 15 with the rear surface placed against the skin of the user 15 such that the electrodes 30 are against the afflicted area; fastening the lower pad 22 around the desired area on the user 15 via the lower pad straps 23 and securing via the securing means 26; removing the controller 50 from the pocket 40; placing batteries 54 into the battery compartment 57 as necessary; depressing the operational switch 51 to activate the apparatus 10; depressing the buttons 52, 53 to a desired setting; positioning the controller 50 into the pocket 40 as desired; enabling the electricity generator 56 to transmit the desired signal to each electrode 30 which contracts the muscles in the desired area on the user 15; and, utilizing the apparatus 10 to provide relief from RLS or similar ailments in a manner which is simple, easy, effective, and comforting.

The foregoing descriptions of specific embodiments have been presented for purposes of illustration and description. They are not intended to be exhaustive or to limit the invention and method of use to the precise forms disclosed. Various modifications and variations can be appreciated by one skilled in the art in light of the above teachings. The embodiments have been chosen and described in order to best explain the principles and practical application in accordance with the invention to enable those skilled in the art to best utilize the various embodiments with expected modifications as are suited to the particular use contemplated. It is understood that various omissions or substitutions of equivalents are contemplated as circumstance may suggest or render expedient, but is intended to cover the application or implementation without departing from the spirit or scope of the claims of the invention.

What is claimed is:

1. An electrical stimulator comprising:
    an upper pad, comprising a planar, elongated elastic member;
    a lower pad, comprising a planar, elongated elastic member; and,
    a controller, further having a power source;
    wherein said upper pad is a discrete and separate unit from said lower pad;
    wherein each said upper pad and said lower pad further comprises:
        a front surface;
        a rear surface adapted to be placed against an afflicted area of a patient;
        a first securing means located on each opposing distal ends of said upper pad for removably securing said upper pad at a first location of said afflicted area;
        a second securing means located on each opposing distal ends of said lower pad for removably securing said lower pad at a second location of said afflicted area;
        a fastening loop located on an intermediate location of said front surface of said of said upper pad;
        an intermediate strap, having a first end with a third securing means for removably connecting to said fastening loop and a second end connected to said front surface of said lower pad;
        a plurality of electrodes integrally molded to said upper pad and said lower pad and comprising an outer portion that protrudes through said rear surface, each of said plurality of electrodes in electrical communication with said controller;
    wherein said first, second, and third securing means are length adjustable; and,
    wherein said intermediate strap further comprises an aperture adapted to permit the routing of electrical wiring from said controller to said lower pad and said upper pad therethrough, said intermediate strap adapted to conceal said electrical wiring;
    wherein said controller generates an electrical impulse and is adapted to transmit said electrical impulse to said afflicted area; and,
    wherein said controller controls an intensity and a duration of said electrical impulse.

2. The electrical stimulator of claim 1, wherein said upper pad and said lower pad each comprise an hourglass-shaped body.

3. The electrical stimulator of claim 2, wherein said upper pad and said lower pad each comprise an elastic material of construction.

4. The electrical stimulator of claim 3, wherein said rear surface further comprises a soft cushioning and padding covering.

5. The electrical stimulator of claim 1, wherein said securing means further comprises a hook-and-loop-type fastener.

6. The electrical stimulator of claim 1, wherein said plurality of electrodes each comprise a cover removably attached to a tacky surface of said outer portion;
    wherein said tacky surface is capable of enabling each of said plurality of electrodes to temporarily adhere to said afflicted area.

7. The electrical stimulator of claim 1, wherein said controller further comprises a generally rectangular housing, further comprising:
    said power source located within said housing;
    a power switch located on an outer surface of said housing and in electrical communication with said power source;
    a control module housed within said housing and in electrical communication with said power switch;
    a generator in electrical communication with said control module;
    an increment button located adjacent to said power switch and in electrical communication with said control module and said generator; and,
    a decrement button located adjacent to said power switch and in electrical communication with said control module and said generator;
    wherein said power switch selectively activates and deactivates said stimulator;
    wherein said generator generates said electrical impulse; and,
    wherein said increment button and said decrement button controls said intensity of said generator.

8. The electrical stimulator of claim 7, wherein a range of said generator is approximately twenty-five volts.

9. An electrical stimulator comprising:
- an upper pad, comprising a planar, elongated elastic member;
- a lower pad, comprising a planar, elongated elastic member;
- a pocket affixed to a front surface of said upper pad; and,
- a controller adapted to be removably inserted within said pocket, further having a power source;
- wherein said upper pad is a discrete and separate unit from said lower pad;
- wherein each said upper pad and said lower pad further comprises:
  - a front surface;
  - a rear surface adapted to be placed against an afflicted area of a patient;
  - a first securing means located on each opposing distal ends of said upper pad for removably securing said upper pad at a first location of said afflicted area;
  - a second securing means located on each opposing distal ends of said lower pad for removably securing said lower pad at a second location of said afflicted area;
  - a fastening loop located on an intermediate location of said front surface of said of said upper pad;
  - an intermediate strap, having a first end with a third securing means for removably connecting to said fastening loop and a second end connected to said front surface of said lower pad;
  - a plurality of electrodes integrally molded to said upper pad and said lower pad and comprising an outer portion that protrudes through said rear surface, each of said plurality of electrodes in electrical communication with said controller;
  - wherein said first, second, and third securing means are length adjustable; and,
  - wherein said intermediate strap further comprises an aperture adapted to permit the routing of electrical wiring from said controller to said lower pad and said upper pad therethrough, said intermediate strap adapted to conceal said electrical wiring;
- wherein said controller generates an electrical impulse and is adapted to transmit said electrical impulse to said afflicted area; and,
- wherein said controller controls an intensity and a duration of said electrical impulse.

10. The electrical stimulator of claim 9, wherein said upper pad and said lower pad each comprise an hourglass-shaped body.

11. The electrical stimulator of claim 10, wherein said upper pad and said lower pad each comprise an elastic material of construction.

12. The electrical stimulator of claim 11, wherein said rear surface further comprises a soft cushioning and padding covering.

13. The electrical stimulator of claim 9, wherein said securing means further comprises a hook-and-loop-type fastener.

14. The electrical stimulator of claim 9, wherein said plurality of electrodes each comprise a cover removably attached to a tacky surface of said outer portion;
- wherein said tacky surface is adapted to enable each of said plurality of electrodes to temporarily adhere to said afflicted area.

15. The electrical stimulator of claim 9, wherein said controller further comprises a generally rectangular housing, further comprising:
- said power source located within said housing;
- a power switch located on an outer surface of said housing and in electrical communication with said power source;
- a control module housed within said housing and in electrical communication with said power switch;
- a generator in electrical communication with said control module;
- an increment button located adjacent to said power switch and in electrical communication with said control module and said generator; and,
- a decrement button located adjacent to said power switch and in electrical communication with said control module and said generator;
- wherein said power switch selectively activates and deactivates said stimulator;
- wherein said generator generates said electrical impulse; and,
- wherein said increment button and said decrement button controls said intensity of said generator.

16. The electrical stimulator of claim 15, wherein a range of said generator is approximately twenty-five volts.

* * * * *